US010847266B1

(12) United States Patent
Ross et al.

(10) Patent No.: US 10,847,266 B1
(45) Date of Patent: Nov. 24, 2020

(54) SYSTEMS AND METHODS FOR TRACKING GOALS

(71) Applicant: MASSACHUSETTS MUTUAL LIFE INSURANCE COMPANY, Springfield, MA (US)

(72) Inventors: Gareth Ross, Amherst, MA (US); Sears Merritt, Groton, MA (US)

(73) Assignee: Massachusetts Mutual Life Insurance Company, Springfield, MA (US)

( * ) Notice: Subject to any disclaimer, the term of this patent is extended or adjusted under 35 U.S.C. 154(b) by 404 days.

(21) Appl. No.: 15/287,590

(22) Filed: Oct. 6, 2016

Related U.S. Application Data

(60) Provisional application No. 62/238,002, filed on Oct. 6, 2015.

(51) Int. Cl.
*G16H 50/30* (2018.01)
*G06Q 50/00* (2012.01)

(52) U.S. Cl.
CPC .............. *G16H 50/30* (2018.01); *G06Q 50/01* (2013.01)

(58) Field of Classification Search
CPC combination set(s) only.
See application file for complete search history.

(56) References Cited

U.S. PATENT DOCUMENTS

| | | | |
|---|---|---|---|
| 2015/0248230 A1* | 9/2015 | Mark | |
| 2016/0078471 A1* | 3/2016 | Hamedi | |
| 2016/0078544 A1* | 3/2016 | Brady | |
| 2016/0314705 A1* | 10/2016 | Segal | |
| 2016/0339300 A1* | 11/2016 | Todasco | |
| 2017/0095716 A1* | 4/2017 | Lewis et al. | |
| 2018/0068083 A1* | 3/2018 | Cohen et al. | |
| 2019/0034494 A1* | 1/2019 | Bradley et al. | |

* cited by examiner

*Primary Examiner* — Michael Tomaszewski
*Assistant Examiner* — William T. Monticello
(74) *Attorney, Agent, or Firm* — Foley & Lardner LLP

(57) ABSTRACT

Disclosed herein are systems and methods for determining and tracking a goal associated with user's health. The method determines a goal of a user. The method generates a goal file based on the goal and generates a social networking campaign file comprising data from the goal file and predetermined criteria for achieving the goal. The method receives social contacts of the user and determines social contacts to invite to the social networking campaign. The method transmits a request to each determined social contact to join the social networking campaign. The method updates the social networking campaign file with data representing the social contacts. The method monitors goal progress data, determines an extent to which the goal progress data satisfies predetermined criteria in the goal file, and generates instructions to update a goal progress score accordingly.

13 Claims, 5 Drawing Sheets

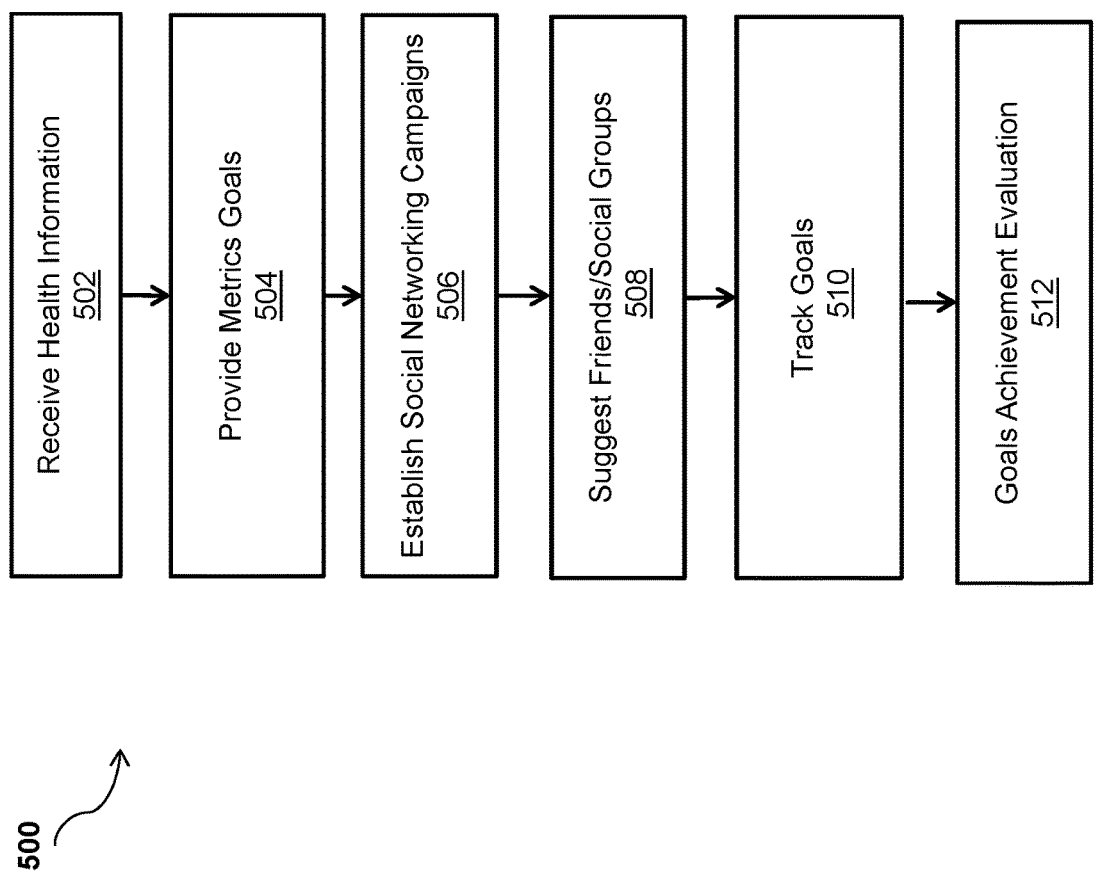

and computing infrastructures. Managing such information on different platforms is difficult due to number, size, content, or relationships of the data associated with the users.
SYSTEMS AND METHODS FOR TRACKING GOALS

CROSS-REFERENCE TO RELATED APPLICATION

This application claims priority to U.S. Provisional Patent Application Ser. No. 62/238,002, filed on Oct. 6, 2015, which is hereby incorporated by reference in its entirety.

TECHNICAL FIELD

The present disclosure relates to systems and methods for using social networking tools in improving, tracking, and achievement of user's goals.

BACKGROUND

As the processing power of computers allow for greater computer functionality and the Internet technology era allows for interconnectivity between computing systems, personal information and data relevant to users' health are more conveniently accessible via the Internet, therefore it is vital to take advantage of this vast array of information. For example, social and business networking sites represent a largely untapped area of potential value for identifying health risks and tracking users' progress to improve said risks. However, existing or conventional methods and systems are generally inefficient in tracking users' goals and consequently ineffective in helping users improve their health risks. Many conventional methods rely on requiring users to undergo health-related testing such as to provide blood and urine samples, or health-related metrics such as blood pressure, weight, height, family diseases history, dependencies, among others in order to track users' risk and goal progress. This process has proven ineffective because of the unreliability of the users' motivation to perform or provide such test results. Other attempts to track the users' goals through online sources have also proven ineffective due to a high volume of information existing on different networks and computing infrastructures. Managing such information on different platforms is difficult due to number, size, content, or relationships of the data associated with the users.

SUMMARY

For the aforementioned reasons, there is a need for a new computer and network-specific process to electronically track users' goals and help users improve their health risk by organizing database records into different sets in order to execute set-specific computing operation.

An embodiment describes a method utilizing social networking for establishing and tracking users' goals, and for helping users achieve these goals. In that embodiment, the method comprises determining a goal of a user to increase a score of the user. The method comprises generating a goal file based on the goal of the user which includes predetermined criteria for achieving the goal. The method comprises generating a social networking campaign file associated with a social networking campaign of the user. The method comprises generating and transmitting an instruction to a social networking site to receive social contacts of the user and then determining social contacts of the user to invite to the social networking campaign of the user. The method comprises transmitting a request to each social contact of the user to join the social networking campaign of the user. The method comprises generating an instruction to update social networking campaign file with data representing each social contact of the user associated with the campaign. The method comprises monitoring the user's goal progress by at least one of the user and the social contacts of the user who associated with the social networking campaign. The method comprises comparing the goal progress with the predetermined criteria for achieving the goal to determine an extent to which the goal progress satisfies the predetermined criteria. The method comprises generating instructions to update a goal progress score based upon the user's progress.

In another embodiment, a computer system comprises determining a goal of a user to increase a score of the user. The computer system comprises generating a goal file based on the goal of the user which includes predetermined criteria for achieving the goal. The computer system comprises generating a social networking campaign file associated with a social networking campaign of the user. The computer system comprises generating and transmitting an instruction to a social networking site to receive social contacts of the user and then determining social contacts of the user to invite to the social networking campaign of the user. The computer system comprises transmitting a request to each social contact of the user to join the social networking campaign of the user. The computer system comprises generating an instruction to update social networking campaign file with data representing each social contact of the user associated with the campaign. The computer system comprises monitoring the user's goal progress by at least one of the user and the social contacts of the user who associated with the social networking campaign. The computer system comprises comparing the goal progress with the predetermined criteria for achieving the goal to determine an extent to which the goal progress satisfies the predetermined criteria. The computer system comprises generating instructions to update a goal progress score based upon the user's progress.

Additional features and advantages of an embodiment will be set forth in the description which follows, and in part will be apparent from the description. The objectives and other advantages of the invention will be realized and attained by the structure particularly pointed out in the exemplary embodiments in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

Non-limiting embodiments of the present disclosure are described by way of example with reference to the accompanying figures which are schematic and are not intended to be drawn to scale. Unless indicated as representing the background art, the figures represent aspects of the disclosure.

FIG. 5 is a flow diagram illustrating an exemplary method for tracking user goals using social networking tools to help users achieve the goals, according to an embodiment.

DETAILED DESCRIPTION

Figure 1:
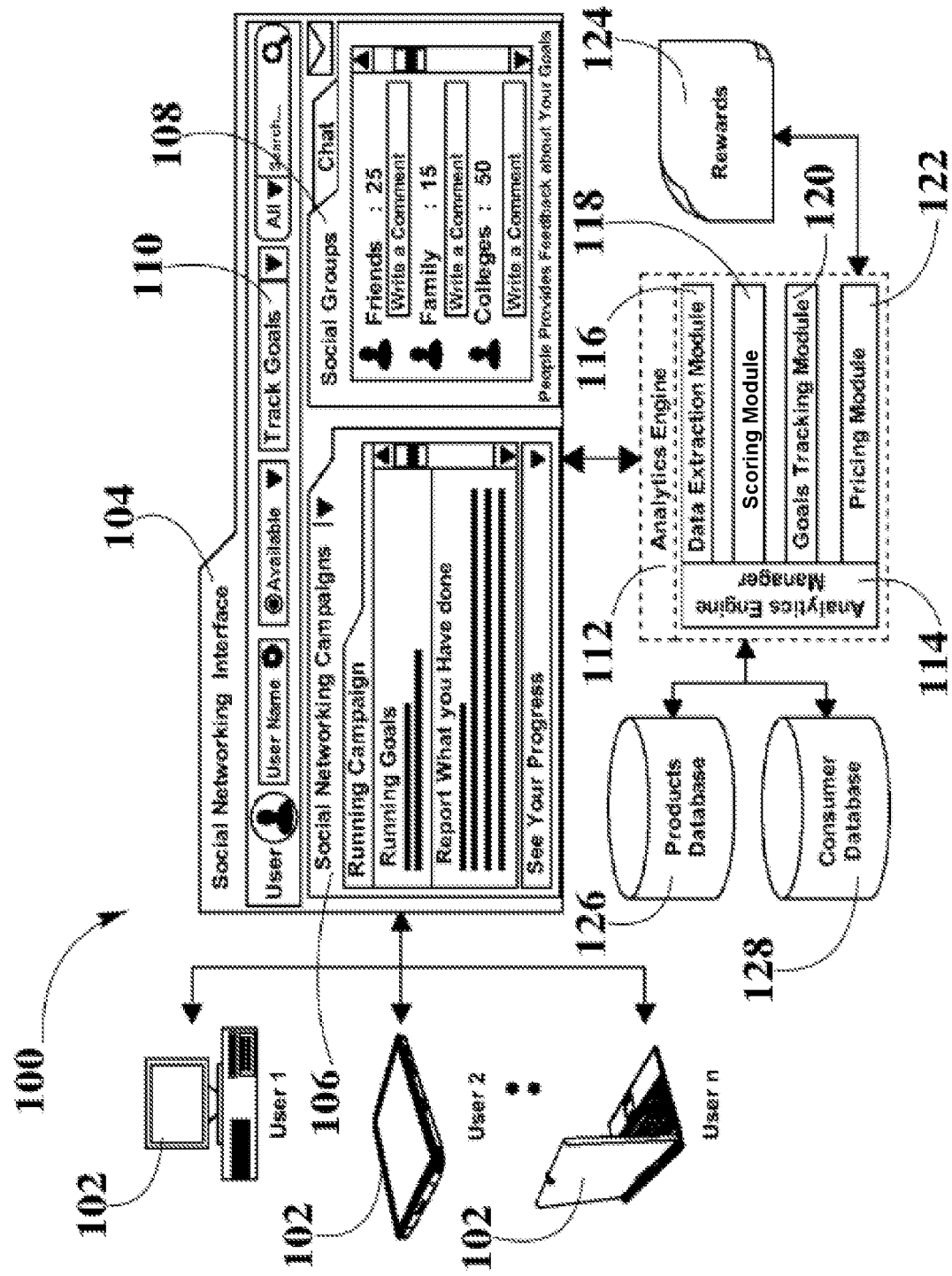
FIG. 1 is a functional block diagram illustrating a system architecture for helping users increase their score, according to an embodiment.

The present disclosure is herein described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here. Furthermore, the various components and embodiments described herein may be combined to form additional embodiments not expressly described, without departing from the spirit or scope of the invention.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

The present disclosure is herein described in detail with reference to embodiments, which form a part here. Other embodiments may be used and/or other changes may be made without departing from the spirit or scope of the present disclosure. The illustrative embodiments described in the detailed description are not meant to be limiting of the subject matter presented here.

The present disclosure describes a system and method for tracking user goals that may help users increase their score using social networking tools. In some embodiments, goal outcomes data indicating successful achievement of user goals results in an increase to the user's score. In some embodiments, goal outcomes data indicating successful achievement of a predetermined level of progress, or milestone, toward a user goal result in a lesser increase to the user's score. In some embodiments, the increase in user's score in turn results in rewards to the user, such as reduced premium, better insurance coverage, and improved benefits.

System Architecture

FIG. 1 is a block diagram illustrating system architecture 100 for tracking user goal to help users increase their score, according to an embodiment. In FIG. 1, system architecture 100 includes different components, for example including a plurality of client computing devices 102, a social networking interface 104, a product database 126, a consumer database 128, an analytics engine 112, and a rewards module 124. In some embodiments, analytics engine 112 includes one or more software modules, such as for example an analytics engine manager 114, a data extraction module 116, an scoring module 118, a goals tracking module 120 and a pricing module 122. In an embodiment, social networking interface 104 includes various tools for tracking data indicating progress of a user toward achievement of user goal (herein called goals progress data). In an embodiment, these tools include social networking campaigns module 106, social groups module 108, and track goals module 110. Social networking interface 104 may include other social networking features, such as chat, multimedia, emails, and the like.

In some embodiments, the different components within system architecture 100 are configured to interact dynamically with each other through a communication network. In these embodiments, the communication network may be implemented as any type of hardware, software, and/or firmware that interconnect and otherwise couple computing devices to allow effective communication between the components of system architecture 100. Communication networks include intranets, local area networks (LAN), virtual private networks (VPN), wireless area networks (WAN) and the World Wide Web, among others.

In FIG. 1, system architecture 100 offers users a set of tools to help them achieve their goals. In some embodiments, analytics engine 112 in system architecture 100 is implemented as one or more computer software modules that include programmatic rules or logic for executing or running different analytics operations. Analytics operations may include, for example, issuing health-related recommendations; providing metrics goals; creating campaigns for goals; extracting user information (e.g., user data, and information on social networks); determining scores; and determining rewards for users. As used in the present disclosure, a "social network" refers to a plurality of individuals and/or entities organized in specific groups, which individuals or entities may interact, collaborate and share knowledge. In other embodiments, analytics engine 112 is configured to help a user track the goal progress towards the achievement of user goal. In some embodiments, upon recognizing the achievement of established user goal, analytics engine 112 determines an increased score for the user. In some embodiments, upon determining an increased score for the user, analytics engine 112 determines one or more rewards for the user such as contacting the score increase to a third-party affiliated with the user. Examples of rewards provided by rewards module 124 include a lower premium and incentives associated with the user's employer. In an embodiment as used in the present disclosure, "benefits" may include financial relief made available by an insurer to a customer that can be used to offset the financial impact the insurer may experience as a result of multiple qualifying events. In an embodiment as used in the present disclosure, a "premium" refers to a non-variable payment required periodically by a company from a customer in order for the company to provide coverage under a given benefits' contract for a defined period of time.

Analytics engine manager 114 of analytics engine 112 may be implemented as one or more computer software modules that include programmatic rules or logic for executing/running different analytics operations to automatically process various types of information. In an embodiment, the analytics engine manager 114 acts as an administrator module of analytics engine 112 that coordinates various operations and processes performed by the analytics engine, such as to determine and select goals, health products/metrics, and to synchronize information between modules. In an embodiment, information processed by analytics engine manager 114 includes medical tests, insurance products, demographic information, and social networking interaction. In an embodiment, information processed by analytics engine manager 114 is obtained from products database 126 and from consumer database 128. Analytics engine manager 114 also coordinates the work of the different software modules in tracking the achievement of user goal of users. In some embodiments, analytics engine manager 114 may include a processing unit for running related algorithms or computer executable program instructions. The processing unit may include a processor with computer-readable medium, such as a random access memory (RAM) coupled to the processor. Examples of processors may include microprocessors, application specific integrated circuits (ASICs) and field programmable object arrays (FPOAs).

In some embodiments, data extraction module 116 in analytics engine 112 is implemented as one or more computer software modules that include programmatic rules or logic for executing, running or retrieving information obtained from a plurality of databases, such as for example product database 126 and consumer database 128. In some embodiments, product database 126 includes information on insurance or health products and beneficial services offered to users. Consumer database 128 includes, for example, demographic information of users, such as for example, gender, age, salary and compensation, marital status, salary, crime record, prescription drug history, home ownership data, medical test data, and dependents, among other information. In some embodiments, data extraction module 116 includes a processing unit for running related algorithms or computer executable program instructions. The processing unit may include a processor with computer-readable medium, such as a random access memory (RAM) coupled to the processor. Examples of processors may include microprocessors, application specific integrated circuits (ASICs) and field programmable object arrays (FPOAs).

In some embodiments, product database 126 is implemented as a relational database that receives information about health products and how the received information is related, stores said information, and retrieves and provides said information to authenticated users. For example, product database 126 may include incentive programs and other related data by user's employer or insurance company. In this embodiment, product database 126 is implemented as conventional database management systems (DBMS), such as, for example MySQL, PostgreSQL, SQLite, Microsoft SQL Server, Microsoft Access, Oracle, SAP, dBASE, FoxPro, IBM DB2, LibreOffice Base, FileMaker Pro, MongoDb and/or any other type of database that may organize collections of data.

In some embodiments, consumer database 128 is implemented as a relational database that receives information about consumers and how the received information is related, stores said received information, and retrieves and provides said information to authenticated users. In these embodiments, consumer database 128 is implemented as conventional database management systems (DBMS), such as, for example MySQL, PostgreSQL, SQLite, Microsoft SQL Server, Microsoft Access, Oracle, SAP, dBASE, FoxPro, IBM DB2, LibreOffice Base, FileMaker Pro, MongoDb and/or any other type of database that may organize collections of data.

In some embodiments, scoring module 118 in analytics engine 112 is implemented as one or more computer software modules that include programmatic rules or logic for executing/running different analytics operations such as performing a risk analysis about users. In these embodiments, scoring module 118 is configured to evaluate the data retrieved by data extraction module 116 (e.g., medical testing, social networking interaction, and products, among others) and perform risk scoring using machine learning techniques such as support vector machine and logistic regression, among others in order to calculate a score of the user. In an example, the risk classification may provide assistance for calculating the likelihood of users to increase their score and may provide insight in maximizing user benefits. In some embodiments, this risk analysis is used by pricing module 122 in setting policy premiums and/or insurance coverage. In some embodiments, scoring module 118 includes a processing unit for running related algorithms or computer executable program instructions. The processing unit may include a processor with computer-readable medium, such as a random access memory (RAM) coupled to the processor. Examples of processors may include microprocessors, application specific integrated circuits (ASICs) and field programmable object arrays (FPOAs).

In other embodiments, goals tracking module 120 within analytics engine 112 is implemented as one or more computer software modules that include programmatic rules or logic for executing/running different analytics operations such as providing metrics goals to users. As used in the present patent application, "metrics goals" mean user goal incorporating health promotion campaigns, e.g., running campaigns, diet campaigns, and doctor controlled campaigns. In an embodiment, metrics goals include health related metrics associated with the health promotion campaign, e.g., blood pressure readings associated with a running campaign; weight measurements associated with a diet campaign; prescription drug history associated with a doctor controlled campaign; and the like.

In an embodiment, user goal are stored as goal files (also herein user goal files, and metrics goal files, in the case of metric goals) in goals tracking module 120. Goal files include attributes representing predetermined criteria for achieving the user goal. In addition, the goal files include data such as user ID; description of the user goal; predetermined criteria for achieving user goal; time frames for achieving user goal; and data on related social networking campaigns. In an embodiment, goal file may include a data for a final user goal including attributes representing predetermined criteria for achieving the final user goal, and may include one or more levels of progress, or milestones, toward the user goal, wherein the goal file would include alternative attributes representing alternative criteria for achieving each such milestone.

In an embodiment, goals tracking module 120 may analyze goals progress data received from a track goals module of social networking interface 104, in combination with data from other sources, to dynamically track users' progress toward successful achievement of user goal. Examples of other data sources for tracking users' progress toward user goal include information provided by users, medical test reports, and information from various databases extracted by data extraction module 120. Collectively, the data received by goals tracking module 120 from various sources and analyzed to dynamically track users' progress toward successful achievement of user goal is herein called "goal progress data." It must be noted that goals tracking module 120 may generate a set of instructions to receive biometric data needed to track user's goals. In an embodiment, data associated with a user (e.g., biometric data) may be stored in a third-party database and goals tracking module 120 may generate/transmit instructions to said database and request the biometric data. For example, a user may independently use wearable health-tracking devices or use a mobile device enabled to track health-related activities and store user's data in an independent and separate database. In that example, goals tracking module 120 may detect such a device using information from the user's social network and generate instructions to receive said data from the third-party database.

In one or more embodiments, wearable health tracking devices are clothing and accessories incorporating computer and advanced electronic technologies. In these embodiments, wearable health tracking devices read biometric data from one or more users, and send biometric data readings from one or more users to an application installed on client computing devices 102. Examples of the biometric data include number of steps per day, heartbeat rates, levels of sweat, O2 saturation, and the like. Client computing devices 102 compute and send biometric data via communication network 112. Examples of wearable health tracking devices include smart watches, trackers, pedometers, activity trackers, and the like. In one embodiment, a client computing device (e.g., smartphone) with the ability to sense and generate biometric data (e.g., number of steps) may be utilized, as well, thereby reducing or eliminating the need for a wearable device.

In an embodiment, goals tracking module 120 generates instruction to an external source (e.g., third-party database) of a wearable health tracking device associated with the user to send data associated the user's activities. Upon receiving this data, goals tracking module 120 processes data received and determines whether they correspond to the goals created. Furthermore, in yet another embodiment, goals tracking module 120 may generate instructions to a health track device to modify health thresholds or biometric tracking behavior. For example, goals tracking module 120 may generate instructions and transmit to a wearable pedometer device and change the user's daily step goal.

In an embodiment, goals tracking module 120 is configured so that successful achievement of a user goal increases the score of users, and goals tracking module 120 is configured to validate if users achieved their user goal. In another embodiment, goals tracking module 120 is configured so that successful achievement of a milestone toward a final user goal increases the score of users by a lesser amount than achievement of the final user goal, and goals tracking module 120 is configured to validate if users achieved their predetermined milestones. In some embodiments, goals tracking module 120 includes a processing unit for running related algorithms or computer executable program instructions. The processing unit may include a processor with computer-readable medium, such as a random access memory (RAM) coupled to the processor. Examples of processors may include microprocessors, application specific integrated circuits (ASICs) and field programmable object arrays (FPOAs).

In an embodiment, based on analysis of goal progress data in view of attributes representing predetermined criteria for achieving a user goal, goals tracking module 120 calculates a goals progress score representing the user's progress toward the user goal (such as a metrics goal). In an embodiment, the analytics engine 112 determines that goal progress data represents successfully achievement of the user goal when the goal progress score equals or exceeds a predetermined threshold. In an example, the analytics engine 112 increases the score of the user by a first amount when the goals progress score exceeds a predetermined threshold indicating successful achievement of a user goal. In another example, the analytics engine 112 increases the score of the user by a second amount lower than the first amount when the goals progress score exceeds an alternative threshold that is lower than the predetermined threshold but that indicates a given level of progress, or milestone, toward successful achievement of the user goal.

An example of a final user goal with a milestone is a running campaign that includes a final user goal of successful completion of three marathons, and successful completion of two marathons as a predetermined milestone toward the final user goal. The goals tracking module also may track a plurality of milestones. An example of a final user goal with two milestones is a weight loss campaign including a predetermined amount of weight loss of the user representing the final user goal, and two lesser predetermined amounts of weight loss, each representing a predetermined milestone toward the final user goal.

Track goals module 110 of social networking interface 104 may interact with analytics engine 112 in various ways to provide dynamic tracking of goals. Track goals module 110 tracks reports goals progress data received from social networking campaigns module 106 and forwards this data to analytics engine 112, which dynamically analyzes this goals progress data via goals tracking module 120 to monitor and determine goal outcomes. In addition, track goals module 110 tracks various goals-related data received from analytics engine 112 and may report this goals-related data to social networking campaigns module 106. Track goals module 110 may receive and track data from goal file received from goals tracking module 120 e.g., at the beginning of a social networking campaign, and goals outcome data received from goals tracking module 120 upon validating a user's successful achievement of a user goal (including final goals and milestones). Track goals module 110 may forward user goal progress data and goals outcome data to social networking campaigns module 106, for publication to members of a related social networking campaign. Additionally, track goals module 110 may receive and may forward to social networking campaigns module 106 goal outcomes assistance data, i.e., data from analytics engine 112 to assist users in improving user scores through achievement of goal outcomes.

In some embodiments, pricing module 122 in analytics engine 112 is implemented as one or more computer software modules that include programmatic rules or logic for executing/running different analytics operation such as generating a price for the new insurance policy to the user, which includes a lower premium and a better coverage of insurance benefits, among other rewards. In FIG. 1, pricing module 122 is configured to analyze and determine the price of an insurance product based on the results obtained from scoring module 118, goals tracking module 120, product database 126 and consumer database 128. In an embodiment, in which pricing module 122 may provide a first increase to the score in the event of successful achievement of a user goal, and a second lesser increase to the score in the event of successful achievement of a milestone toward the user goal, pricing module 122 may determine different improved prices in these respective events. The pricing module 122 may handle data integration, break data streams into parts, and execute rules, among other functions. In an embodiment, pricing module 122 may include components for setting the premium of a pooled insurance benefit product. In some embodiments, pricing module 122 includes a processing unit for running related algorithms or computer executable program instructions. The processing unit may include a processor with computer-readable medium, such as a random access memory (RAM) coupled to the processor. Examples of processors may include microprocessors, application specific integrated circuits (ASICs) and field programmable object arrays (FPOAs).

In FIG. 1, system architecture 100 includes social networking interface 104, which may be displayed in one or more client computing devices 102. The displayed graphical social networking interface 104 includes one or more social networking tools, such as for example, social networking campaigns module 106, social groups module 108, and track goals module 110, which are configured to receive information from one or more users. In some embodiments, analytics engine 112 through social networking interface 104, allows users to improve their coverage of benefits and/or insurance product, as well as to have a lower premium. In an example, analytics engine 112 analyzes information, such as for example, goals achieved by the users, social networking reports, consumer data, and products data, among others.

In some embodiments, social networking interface 104 is implemented as one or more software modules configured to display one or more social features on client computing devices 102. Social features in social networking interface 104 includes tracking progress, email, multimedia, and chat, among others. Examples of client computing devices 102 may include smartphones, desktop computers, laptop computers, tablets, and PDAs, among others.

In yet other embodiments, social networking campaigns module 106 in social networking interface 104 is implemented as one or more software modules configured to allow users to join different campaigns based on their profile, group of friends, goals, and metrics, among others. Social networking campaigns module 106 may include different strategies for tracking goals, such as running campaigns, weight watchers campaigns, diet campaigns, doctor controlled campaigns, and a health monitoring device implemented for tracking goals, among others. Social networking campaigns module 106 maintains a database of social networking campaign files, including a social networking campaign file for each social networking campaign of a given user. Social networking campaign files 106 include data such as identifications of users and user social contacts participating in given social networking campaigns; goals progress data; data concerning user goal including significant milestones toward user goal; data concerning social media included in social networking campaigns; goal metrics data; among others. In one embodiment, social networking campaign module may send goal progress data including a recommendation of successful achievement of a user goal (goal outcomes) to goals tracking module 120 of analytics engine 112, subject to validation of goal outcomes by analytics engine 112.

Social networking campaigns provide various benefits in pursuing and achieving user goal. Social networking campaign participants can influence and encourage users to achieve user goal, including final user goal and milestones. Social networking campaign participants may have experience and/or expertise in campaign goals, and may provide advice to help users make progress toward user goal. Social networking campaigns can be a significant current source of goals progress data, which may be forwarded by social networking interface 104 to analytics engine 112 for dynamically tracking goals progress. In addition, social networking campaigns module 106 may receive goals-related data such as a goal file (or data extracted from that file) and goals outcome data from analytics engine 112, via track goals module 110. Social networking campaigns module 106 may publish this goals-related data to social networking campaign participants. Acting on this goals-related data, social networking campaign participants can encourage and counsel users to achieve user goal, and can provide meaningful recognition of user achievements in the event of successful goal outcomes. Additionally, social networking campaign participants may encourage and counsel users to make progress toward user goal based upon goal outcomes assistance data received by track goals module 110 from analytics engine 112.

Social groups module 108 in social networking interface 104 is implemented as one or more software modules configured to allow users participating in a campaign to manually or automatically select, through social networking interface 104, those friends, colleagues, neighbors, family members or any other individual who may be interested in joining the same campaign in order to encourage and help the user to achieve his/her goals.

Track goals module 110 in social networking interface 104 is implemented as one or more software modules configured to allow the user to see his/her goals progress, update goals progress, add goals, eliminate goals, report goals progress, see a list of goals, and develop goals progress graphs, among others. In some embodiments, track goals module 110 tracks users' progress in achieving user goal via goal outcomes data. In some embodiments, track goals module provides goals progress data to goals tracking module 120 within analytics engine 112, to monitor the goals progress data to detect and/or validate a goal outcome (a final goal, or a significant milestone). In some embodiments, the goals tracking module 120 within analytics engine 112 reports goal outcomes data representing achievement of a user goal or milestone back to the track goals module 110 in social networking interface 104. Track goals module 110 may in turn forward goal outcomes data to social networking campaigns module 106. In an embodiment, social networking campaign module 106 reports validated achievements of goal outcomes to users and to participating members of user social groups 108 included in pertinent social networking campaign files. In some embodiments, social networking interface 104 displayed on client computing devices 102 exhibits intelligent features supporting human-computer interactions to increase the score of users. In other embodiments, social networking interface 104 may act as a single portal for accessing to the different social networking tools.

Figure 2:
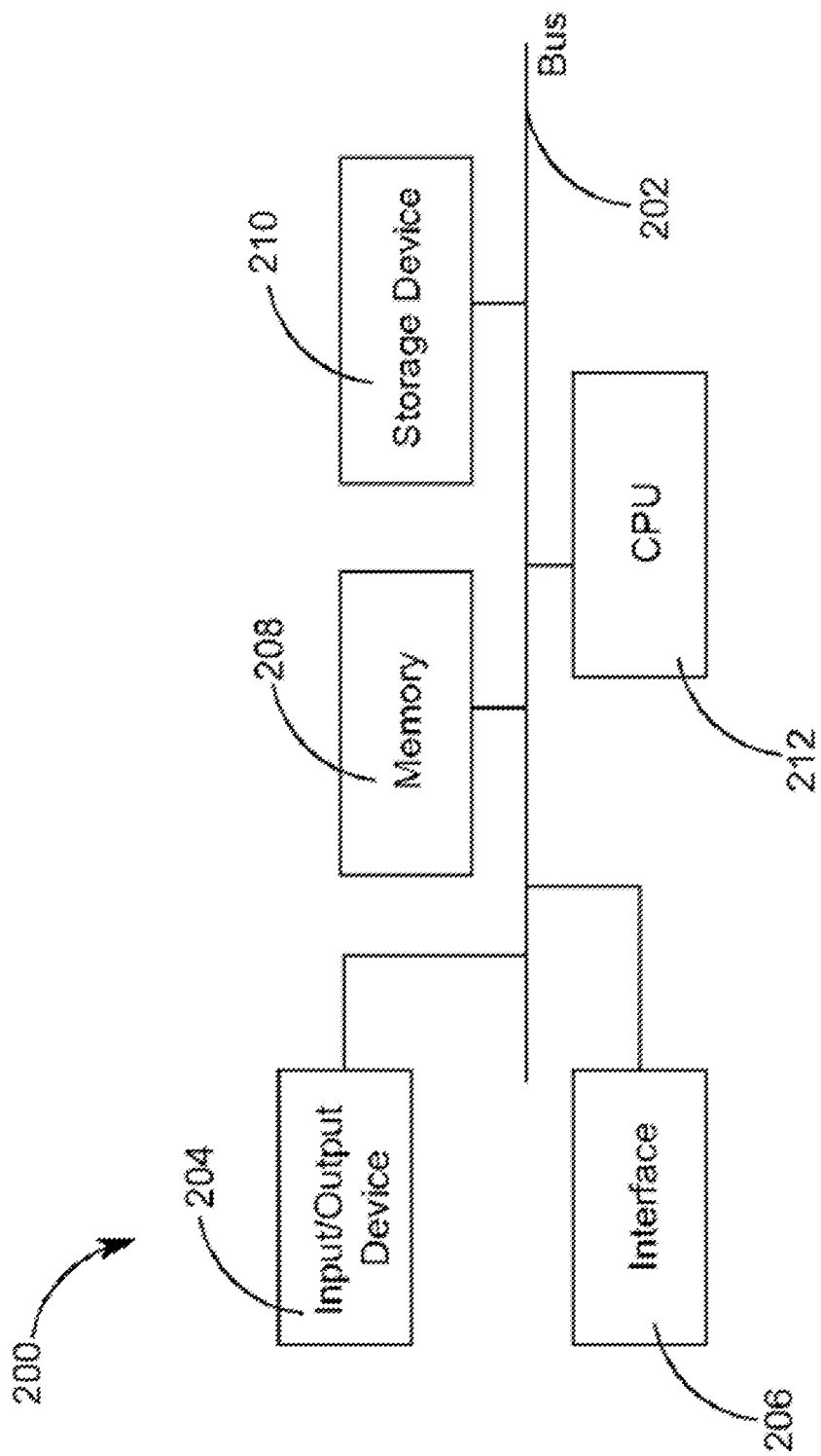
FIG. 2 is a functional block diagram illustrating an exemplary computing device for a system for helping users increase their score, according to an embodiment.

FIG. 2 is a block diagram illustrating an exemplary computing device in which one or more embodiments of the present disclosure operate. According to some aspects of this embodiment, computing device 200 includes a bus 202, an input/output device 204, a communication interface 206, a memory 208, a storage device 210, and a central processing unit 212. In another embodiment, computing device 200 may include additional, fewer, different, or differently arranged components than those illustrated in FIG. 2.

Bus 202 may include a path that permits components within computing device 200 to communicate with each other. Input/output device 204 may include peripherals and/or other mechanisms that may enable a user to input information to computing device 200, including a keyboard, computer mice, buttons, touch screens, voice recognition, and biometric mechanisms, among others. Input/output device 204 may also include a mechanism that outputs information to the user of computing device 200, such as, a display, a light emitting diode (LED), a printer, and a speaker, among others.

Communication interface 206 may include mechanisms that enable computing device 200 to communicate with other computing devices and/or systems through a communication network. Communication network may refer to any connections between computers, such as, intranets, local area networks (LAN), virtual private networks (VPN), wireless area networks (WAN), and the internet, among others. Memory 208 may include a random access memory (RAM) or another type of dynamic storage device that may store information and instructions for execution by central processing unit 212. Storage device 210 may include a magnetic and/or optical recording medium, such as read-only memory, flash memory, ferro-electric RAM (F-RAM) hard disks, solid-state drives, floppy disks, and optical discs, among others. Central processing unit 212 may include various devices that interpret and execute instructions, such as a microprocessor, an application specific integrated circuit (ASIC), and a field programmable object array (FPOA), among others.

In some embodiments, the system architecture includes at least one computing device 200, such as a server, a client computing device, a smartphone, a desktop computer, a laptop computer, a tablet computer, a PDA, and/or another type of processor-controlled device. Computing device 200 may receive, process, and/or transmit digital data, among others, and may perform various operations appropriate to an insurance product processing system. The computing device(s) 200 may perform these operations in response to central processing unit 212 executing software instructions contained in a computer-readable medium, such as memory 208.

The software instructions may be read into memory 208 from another computer-readable medium, such as storage device 210, or from another computing device via communication interface 206. The software instructions contained in memory 208 may cause central processing unit 212 to perform processes that may be described later. Alternatively, hardwired circuitry may be used in place of or in combination with software instructions to implement processes described here. Thus, implementations described here are not limited to any specific combination of hardware circuitry and software.

Figure 3:
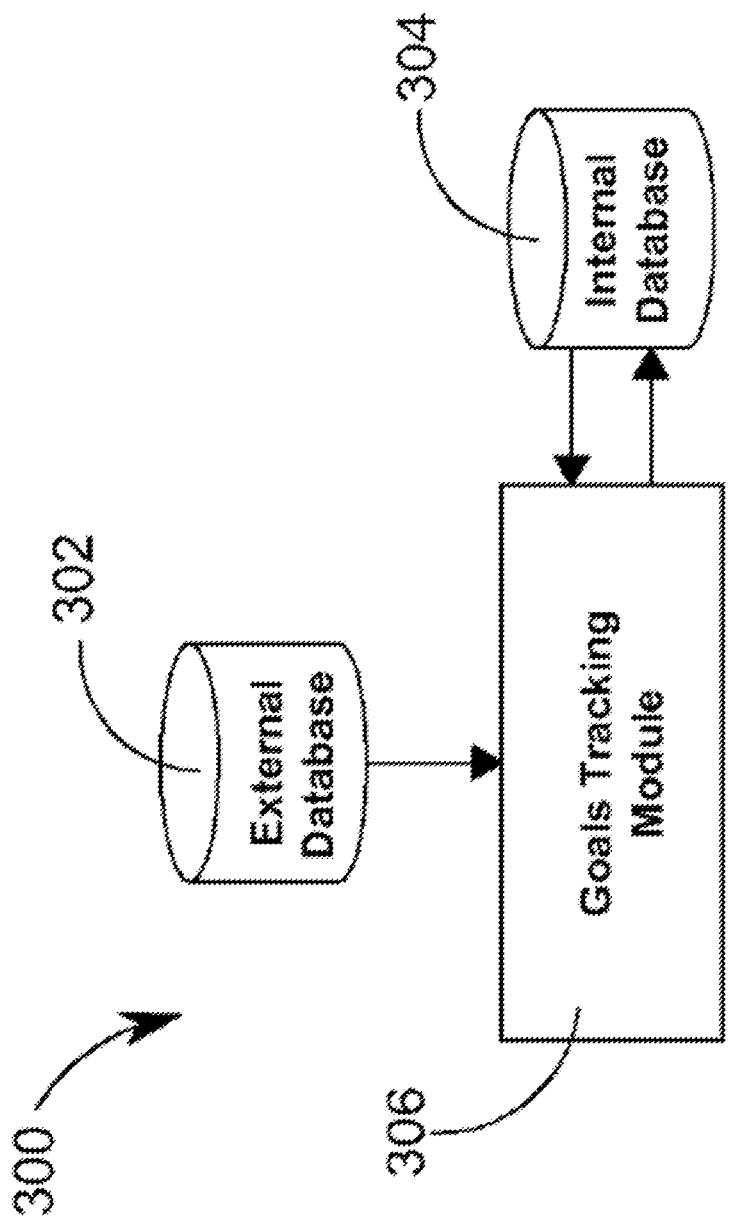
FIG. 3 is functional block diagram illustrating a system subassembly, according to an embodiment.

FIG. 3 is functional block diagram 300 illustrating a portion of the system architecture for tracking user goal of users, according to an embodiment. In FIG. 3, block diagram 300 includes different components that dynamically interact with each other through a communication network, such as for example, external database 302, internal database 304, and goals tracking module 306. It should be understood that block diagram 300 can include less components, more components, or different components depending on the desired analysis goals. In an example and referring to FIG. 1, said goals tracking module 306 is implemented as goals tracking module 120 in system architecture 100. In FIG. 3, goals tracking module 306 is operatively coupled to and in communication with external database 302 (implemented in FIG. 1 as products database 126 and consumer database 128) and internal database 304.

In some embodiments, goals tracking module 306 is implemented as one or more software modules that include programmatic rules or logic for executing/running different user interfaces for gathering user data, estimating a user's behavioral profile, estimating user's preferences, financial information, demographic information, and the like. In these embodiments, Goals tracking module 306 is configured to monitor and validate if a user increases the score during a period of one year based on the achievement of goals (e.g., improving health condition) assigned by the goals tracking module 306. In other embodiments, the goals assigned to a user can be implemented by an analytics engine through goals tracking module 306, which may include social network campaign (e.g., running campaigns, diet campaigns, doctor controlled campaigns, and the like), the use of a health monitoring device to control the blood pressure, heart beat, blood sugar levels, and the like. In yet other embodiments, the information collected from these aforementioned goals (achieved by the user) may be stored in internal database 304 and used by a third-party company for scoring purposes.

Figure 4:
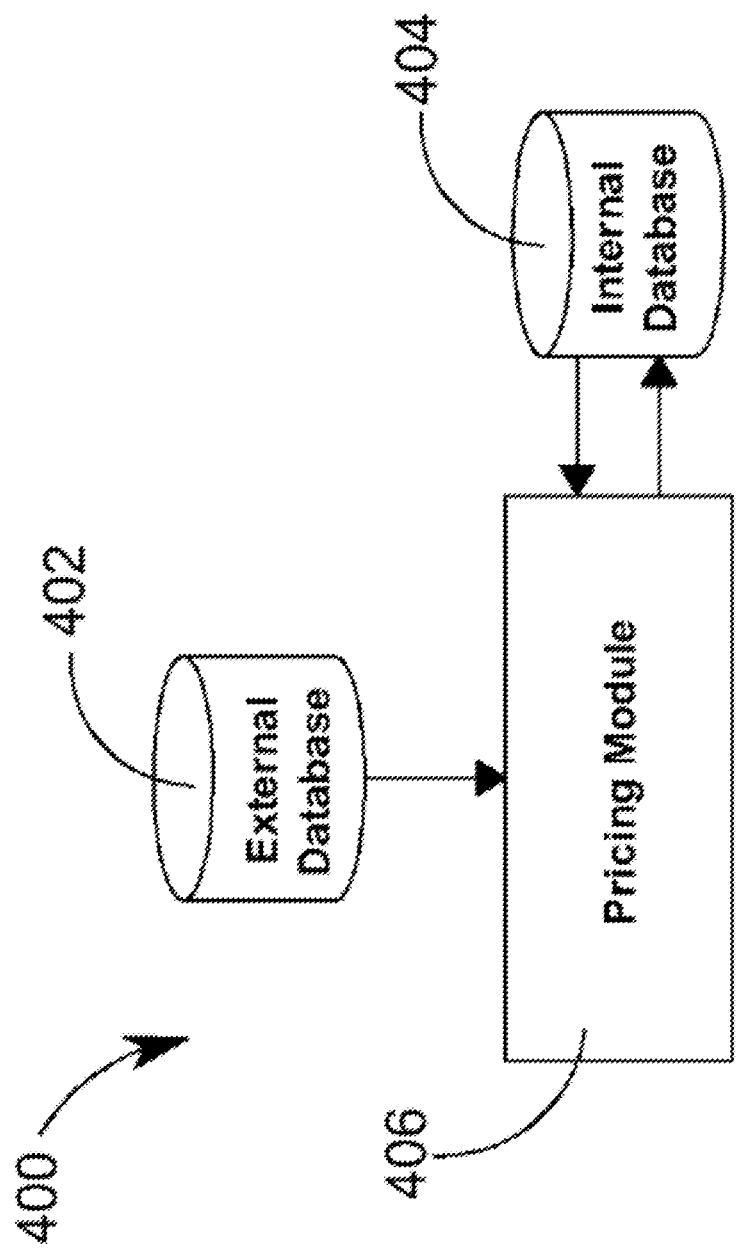
FIG. 4 is a functional block diagram of another system subassembly, according to an embodiment.

FIG. 4 is a functional block diagram 400 of yet another portion of the system architecture, pertaining to pricing. In FIG. 4, block diagram 400 includes different components that dynamically interact with each other through a communication network, such as for example, external database 402, internal database 404, and pricing module 406. It should be understood that block diagram 400 can include less components, more components, or different components depending on the desired analysis goals. In an embodiment, pricing module 406 is implemented as pricing module 122 in the system architecture 100 of FIG. 1. In FIG. 4 pricing module 406 is operatively coupled to and in communication with external database 402 (implemented in FIG. 1 as products database 126 and consumer database 128) and internal database 404.

In some embodiments, pricing module 406 is implemented as one or more software modules that include programmatic rules or logic for executing/running different user interfaces for gathering user data, estimating a user's behavioral profile, estimating user's preferences, financial information, demographic information, and the like. In these embodiments, the information obtained in the goals tracking module (shown in FIG. 3) allows pricing module 406 to calculate and determine rewards, such as, for example lower premium insurance coverage and other health incentives that may be offered by the user's employer, and the like. In some embodiments, information calculated by the pricing module 406 regarding benefits or rewards are stored in internal database 404.

Method for Tracking User Goal

One or more computing devices, such as computing device 200, may perform a plurality of methods for tracking user goals using social networking tools, which may increase the score of users. In some embodiments, the methods are implemented with components of the exemplary operating environments of FIGS. 1-4. The steps of this exemplary process 500 are embodied in a computer readable medium containing a computer readable code such that the steps are implemented when the computer readable code is executed by a computing device. While the blocks in the disclosed process are shown in a particular order, the actual order may differ. In some embodiments, some steps may be performed in parallel.

FIG. 5 is a flow diagram of a process 500 for tracking goals in a social networking context in order to help a user achieve his/her goal, in order to increase the user's score, according to an embodiment. In an embodiment as seen in FIG. 5 process 500 starts at step 502 when the analytics engine included within a system architecture receive health information or goals. In other embodiments, a process 500 includes the user authorizes analytics engine to receive health-related information from variety of sources associated with the user.

In some embodiments, a social networking interface allows analytics engine to perform self-reports about user information (e.g., medical tests, credit cards or financial reports, social, and demographic information). In other embodiments, the analytics engine uses different tools which may be displayed on the social networking interface. Examples of such tools include social networking campaigns module, social groups module, and goals tracking module.

In step 504, a goals tracking module may establish metrics goals for users. In some embodiments, an analytics engine is configured to establish metrics goals (e.g., running campaigns or the like) for one or more users. In an embodiment, the metrics goals are to be achieved within a defined period of time. In an embodiment, the metrics goals are to be achieved within a one from the start date, and allow users to increase their score during that one year period.

In step 506, analytics engine may provide one or more social networking campaigns to a user. In some embodiments, social networking campaigns include running campaigns; weight watchers campaigns; diet campaigns; doctor controlled campaigns; and health monitoring devices used to control blood pressure, heartbeat, blood sugar levels, and the like; among others. In these embodiments, the one or more social networking campaigns are used for tracking the user's progress in achieving user goal, i.e., the social networking campaigns provide goal outcomes data. In an example, if a user wants to lose eight pounds, she/he may sign up, through the social networking campaigns module, for a running campaign in which she/he aims to jog a mile per day. The social networking interface may track goals progress as an aspect of the running campaign, to help the user achieve this weight-loss goal. Process 500 then advances to step 508.

In step 508, the analytics engine, through the social networking interface, allows users to invite, suggest, select or email any individual(s) (e.g., friends, colleagues, neighbor, and family members) to join the social networking campaign. In some embodiments, at step 508 the analytics engine may automatically invite individuals or social groups within social groups module that are part of the user's social network to participate in the social networking campaign, encouraging the user to achieve his/her goal. For example, the analytics engine may invite all members of the user's social network included in the social groups database, or alternatively the analytics engine may invite selected members of the user's social network based upon criteria such as known affinity to user goal, and prior or current participation in other social networking campaigns.

In step 510, the analytics engine allows one or more users to track their goals. In some embodiments, a track goals module within the social networking interface includes customizable features for tracking goals and displaying the goals tracking. In an example, such features include updating goals progress, adding goals, eliminating goals, creating lists of goals, reporting goals progress, and displaying graphical representations of goals progress such as graphs and charts, and similar features. In some embodiments, in step 510 the user's employer stores and reports the goals tracking progress of users. The goals tracking progress reports may be based on various information, such as emails, pictures, and other shared information of social groups; social networking campaigns ranking; and health related metrics such as prescription drug history, among others.

In step 512, the analytics engine may evaluate the goals achievement of users based on the goals tracking reports. In step 512, a data extraction module within the analytics engine may retrieve information from various databases, such as the product databases (e.g., health insurance products, retirement services), and consumer databases (e.g., medical tests, crime records, prescription drug history, and demographic information). Additionally, the analytics engine may retrieve information from modules of the social networking interface. In some embodiments, the retrieved information may result from interaction of the social groups module, social networking campaigns module, and tracking goals module.

In an embodiment, an analytics engine manager may provide the goal achievement evaluations to the scoring module for performing risk analysis for users. In these embodiments, the scoring module may evaluate the data retrieved by data extraction module and perform risk scoring. In an embodiment, the risk scoring uses machine learning techniques such as support vector machine (SVM) algorithms, and logistic regression, among others. In other embodiments, the analytics engine may provide information to users for calculating the likelihood of improving their score; herein this information is called "goal outcomes assistance data". In further embodiments, selected goal outcomes assistance data from the analytics engine may be forwarded to the social networking interface and may be published to participants in a social networking campaign so that campaign participants may counsel users on this information. In various embodiments, the analytics engine manager may provide the outcome from the scoring module to the pricing module to calculate and determine, through analytics, rewards offered to users. In an example, the rewards include lower premiums and/or higher insurance coverage. In some embodiments, the pricing module takes into account one or more criteria when performing calculations and determinations. Examples of such criteria include the maximum benefits, the accrual schedule, the premium payment schedule, and the premium of each of the insurance benefits, among others. In another embodiment, the analytics engine provides a health-related insurance policy (e.g., a policy associated with the user's new score) to the user using the information obtained and the new score.

In some embodiments, by executing process 500 through the exemplary operating environments shown in FIGS. 1-4, data analytics and data mining techniques can be implemented for faster, more efficient processing of large data sets. In this way, efficiencies are created by providing the users with ways to automatically increase the score of users through the implementation of different tools that provide information (physical or health information) of the goals achieved by the user in a social network. In addition, the users or other interested third-parties can automatically receive the information of the goals tracking achieved by the user (e.g., blood samples, blood pressure, and the like) and other information through communication network, which is used for decision making. These features allow performing large work such as voluminous calculations in a more efficient manner than traditional approaches such as manual analyses.

While various aspects and embodiments have been disclosed, other aspects and embodiments are contemplated. The various aspects and embodiments disclosed are for purposes of illustration and are not intended to be limiting, with the true scope and spirit being indicated by the following claims.

The foregoing method descriptions and the interface configuration are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

What is claimed is:
1. A computer-implemented method comprising:
    generating, by the processor of the analytics engine server, a goal file representing a goal to increase a risk classification of a user, based at least in part on selections received from a user device, wherein the goal file includes attributes for achieving a user goal and a predetermined threshold for the user goal, the attributes representing predetermined criteria for achieving the user goal;
    generating, by the processor of the analytics engine server, a social networking campaign file associated with a social networking campaign of the user based at least in part on data received from the user device, the social networking campaign file comprising the attributes representing the predetermined criteria for achieving the user goal and health-related metrics associated with the social networking campaign;
    querying, by the processor of the analytics engine server, one or more social groups databases to receive social contacts of the user, and determining, by the processor of the analytics engine server, social contacts of the user to invite to the social networking campaign of the user;
    transmitting, by the processor of the analytics engine server, a request to each determined social contact of the user to associate with the social networking campaign of the user;
    updating, by the processor of the analytics engine server, the social networking campaign file with data representing each determined social contact of the user who associated with the social networking campaign;
    monitoring, by the processor of the analytics engine server, the social networking campaign file to detect transmission to the social networking campaign file of goal progress data associated with the user by the social contacts of the user who associated with the social networking campaign and to detect transmission of biometric data readings from a health-tracking device worn by the user, wherein the biometric data readings are selected from the group consisting of heartbeat rate, levels of sweat, steps per day and oxygen saturation reading;
    in response to receiving the transmission to the social networking campaign file of the goal progress data associated with the user and to receiving the transmission of the biometric data readings from the health-tracking device worn by the user, applying, by the processor of the analytics engine server, a predictive machine learning model by applying one or more of support vector machine algorithms and logistic regression to the goal progress data associated with the user and the biometric data readings from the health-tracking device worn by the user to determine a risk score, wherein the predictive machine learning model was previously trained by performing risk classification analysis on medical testing data and social networking interaction data retrieved by a data extraction module to calculate the risk score representing likelihood of improving the attributes representing the predetermined criteria for achieving the user goal;
    in response to the predictive machine learning model determining the risk score, updating a goal progress score tracked by a goals tracking module based on the risk score, and updating goal progress data tracked by the goal tracking module based on the goal progress data associated with the user based on the transmission to the social networking campaign file; and
    in the event the goal progress score tracked by the goals tracking module exceeds the predetermined threshold for the user goal and the goal progress data tracked by the goals tracking module satisfies the attributes rep- resenting the predetermined criteria for achieving the user goal, displaying, by the processor of the analytics engine server, an increased risk classification on a user interface of the user device.

2. The method step of claim 1, wherein the attributes representing the predetermined criteria for achieving the user goal include an attribute representing a time limit for achieving the user goal.

3. The method step of claim 1, further comprising generating and transmitting an instruction, by the processor of the analytics engine server, to a database associated with the health-tracking device worn by the user in order to receive the biometric data readings.

4. The method of claim 1, further comprising the step, by the analytics engine of the processor of the analytics engine server, of displaying goal outcomes assistance data on the user interface of the user device, wherein the goal outcomes assistance data includes information on increasing the score of the user.

5. The method of claim 1, wherein the goal file includes attributes for achieving a final user goal and a predetermined threshold for the final goal, and alternative attributes for achieving a milestone user goal and a predetermined threshold for the milestone user goal that is lower than the predetermined threshold for the final user goal; wherein the attributes represent predetermined criteria for achieving the final user goal and the alternative attributes represent predetermined alternative criteria for achieving the milestone user goal; wherein the social networking campaign file includes the attributes representing the predetermined criteria for achieving the final user goal, the alternative attributes representing the predetermined alternative criteria for achieving the milestone user goal, and the health related metrics associated with the social networking campaign.

6. The method of claim 5, wherein the increased risk classification comprises a first increased risk classification; wherein in the event the goal progress score tracked by the goals tracking module exceeds the predetermined threshold for the final user goal, and the goal progress data tracked by the goals tracking module satisfies the attributes for achieving the final user goal, displaying, by the processor of the analytics engine server, the first increased risk classification on the user interface of the user device.

7. The method of claim 6, wherein the increased risk classification comprises the first increased risk classification and a second increased risk classification lower than the first increased risk classification; wherein in the event the goal progress score tracked by the goals tracking module exceeds the predetermined threshold for the milestone user goal, and the goal progress data tracked by the goals tracking module satisfies the alternative attributes for achieving the milestone user goal, displaying, by the processor of the analytics engine server, the second increased risk classification on the user interface of the user device.

8. The method of claim 5, wherein the increased risk classification comprises a second increased risk classification; wherein in the event the goal progress score tracked by the goals tracking module exceeds the predetermined threshold for the milestone user goal, and the goal progress data tracked by the goals tracking module satisfies the alternative attributes for achieving the milestone user goal, displaying, by the processor of the analytics engine server, the second increased risk classification on the user interface of the user device.

9. The method of claim 1, further comprising the step, in the event the goal progress score tracked by the goals tracking module exceeds the predetermined threshold for the user goal, and the goal progress data tracked by the goals tracking module satisfies the attributes representing the predetermined criteria for achieving the user goal, of determining and displaying on the user interface of the user device, one or more of reduced premium and improved coverage based upon the increased risk score.

10. The method of claim 1, wherein in the step of applying the predictive machine learning model, the predictive machine learning model was previously trained by performing risk classification analysis on the medical testing data, the social networking interaction data, and on products data retrieved by the data extraction module to calculate the risk score representing likelihood of improving the attributes representing the predetermined criteria for achieving the user goal.

11. A computer-implemented method comprising:
generating, by the processor of the analytics engine server, a goal file representing a goal to increase a risk classification of the a user, based at least in part on selections received from a user device; wherein the goal file includes attributes for achieving a user goal and a predetermined threshold for the user goal, the attributes representing predetermined criteria for achieving the user goal;
generating, by the processor of the analytics engine server, a social networking campaign file associated with a social networking campaign of the user based at least in part on data received from the user device, the social networking campaign file comprising the attributes representing the predetermined criteria for achieving the user goal and health related metrics associated with the social networking campaign;
querying, by the processor of the analytics engine server, one or more social groups databases to receive social contacts of the user, and determining, by the processor of the analytics engine server, social contacts of the user to invite to the social networking campaign of the user;
transmitting, by the processor of the analytics engine server, a request to each determined social contact of the user to associate with the social networking campaign of the user;
updating, by the processor of the analytics engine server, the social networking campaign file with data representing each determined social contact of the user who associated with the social networking campaign;
monitoring, by the processor of the analytics engine server, goal progress data associated with the user based on a transmission to the social networking campaign file to detect transmission to the social networking campaign file of goal progress data associated with the user by the social contacts of the user who associated with the social networking campaign, and to receive health-related goal progress data from a health-tracking device worn by the user, wherein the health-related goal progress data comprises biometric data readings;
in response to receiving the transmission to the social networking campaign file of the goal progress data associated with the user and to receiving the health-related goal progress data from the health-tracking device worn by the user, executing, by the processor of the analytics engine server, a predictive machine learning model configured to determine a risk score by applying one or more of support vector machine algorithms and logistic regression to each of the goal progress data associated with the user based on the transmission to the social networking campaign file and the health-related goal progress data from the health-tracking device worn by the user, wherein the predictive machine learning model was previously trained by performing risk classification analysis on medical testing data and social networking interaction data retrieved by a data extraction module to calculate the risk score correlating health related metrics with likelihood of improving the attributes representing the predetermined criteria for achieving the user goal;

in response to the predictive machine learning model determining the risk score, updating a goal progress score tracked by a goals tracking module based on the risk score determined by the predictive machine learning model, and updating goal progress data tracked by the goal tracking module based on the goal progress data associated with the user based on the transmission to the social networking campaign file; and in the event the goal progress score tracked by the goals tracking module exceeds the predetermined threshold for the user goal and the goal progress data tracked by the goals tracking module satisfies the attributes representing the predetermined criteria for achieving the user goal, displaying, by the processor of the analytics engine server, an increased risk classification on a user interface of the user device.

12. The method of claim 11, further comprising generating and transmitting an instruction, by the processor of the analytics engine server, to a database associated with the health-tracking device worn by the user in order to receive the health-related goal progress data.

13. The method of claim 11, wherein the biometric data readings are selected from the group consisting of heartbeat rates, levels of sweat, steps per day and oxygen saturation readings.

* * * * *